United States Patent [19]

Kersten et al.

[11] Patent Number: 5,020,162

[45] Date of Patent: Jun. 4, 1991

[54] GLOVE

[75] Inventors: Jean Kersten, Villers St. Amand; Etienne Lombard, Genappe; Daniel Heindrichs, Waimes, all of Belgium

[73] Assignee: Baxter International Inc., Deerfield, Ill.

[21] Appl. No.: 435,531

[22] PCT Filed: Mar. 29, 1989

[86] PCT No.: PCT/US89/01300

§ 371 Date: Nov. 22, 1989

§ 102(e) Date: Nov. 22, 1989

[87] PCT Pub. No.: WO89/08995

PCT Pub. Date: Oct. 5, 1989

[30] Foreign Application Priority Data

Apr. 1, 1988 [BE] Belgium .................... 08800385

[51] Int. Cl.$^5$ .................... A41D 19/00
[52] U.S. Cl. .................... 2/164; 2/168
[58] Field of Search ........... 2/159, 164, 165, 167, 2/168, 169, 260, 260.1, 163, 161 R; 604/349

[56] References Cited

U.S. PATENT DOCUMENTS

| | | | |
|---|---|---|---|
| 2,586,674 | 2/1952 | Lonne | 604/349 |
| 3,110,035 | 11/1963 | La Hue | 2/168 |
| 3,225,360 | 12/1965 | Keilen, Jr. et al. | 2/167 |
| 3,625,790 | 12/1971 | Ayres | 2/159 X |
| 3,633,216 | 1/1972 | Schonholtz | 2/168 |
| 3,866,245 | 2/1975 | Sutherland | 2/162 X |
| 3,874,000 | 4/1975 | Attman | 2/164 X |
| 4,027,060 | 5/1977 | Esemplare et al. | 2/168 X |
| 4,070,713 | 1/1978 | Stockum | 2/168 |
| 4,082,862 | 4/1978 | Esemplare et al. | 2/168 X |
| 4,143,423 | 5/1979 | Sternlieb | 2/168 |
| 4,197,592 | 4/1980 | Klien | 2/164 X |
| 4,310,928 | 1/1982 | Joung | 2/168 X |
| 4,668,224 | 5/1987 | Lentz et al. | 2/168 X |
| 4,679,257 | 7/1987 | Town | 2/159 X |
| 4,881,277 | 11/1989 | Hogle | 2/161 X |
| 4,919,966 | 4/1990 | Shlenker | 2/168 X |

Primary Examiner—William A. Cuchlinski, Jr.
Assistant Examiner—Scott Cummings
Attorney, Agent, or Firm—Kay H. Pierce; Paul C. Flattery

[57] ABSTRACT

A glove comprising a front sheet (9) and a back sheet (10). At least one of the sheets consists of an outer layer (12) and an inner layer (13) made of polymeric films. The layers are bound to each other. The faces (18) facing each other of at least two adjacent layers (12, 13) are independent from each other so as to allow relative movement (M) between the two layers (12, 13).

9 Claims, 5 Drawing Sheets

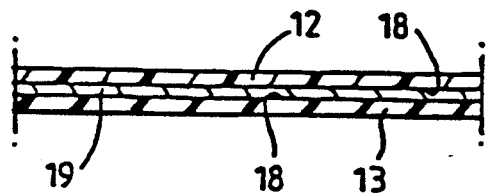
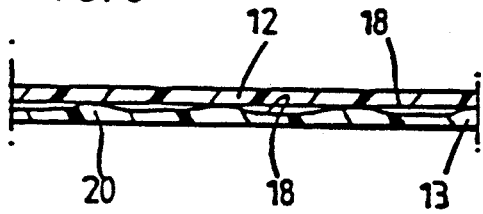
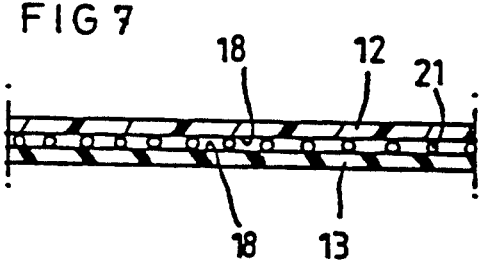
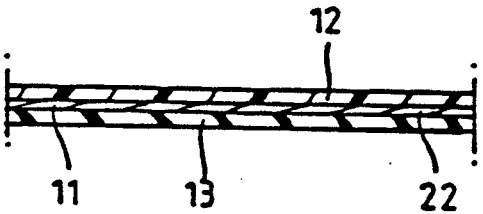
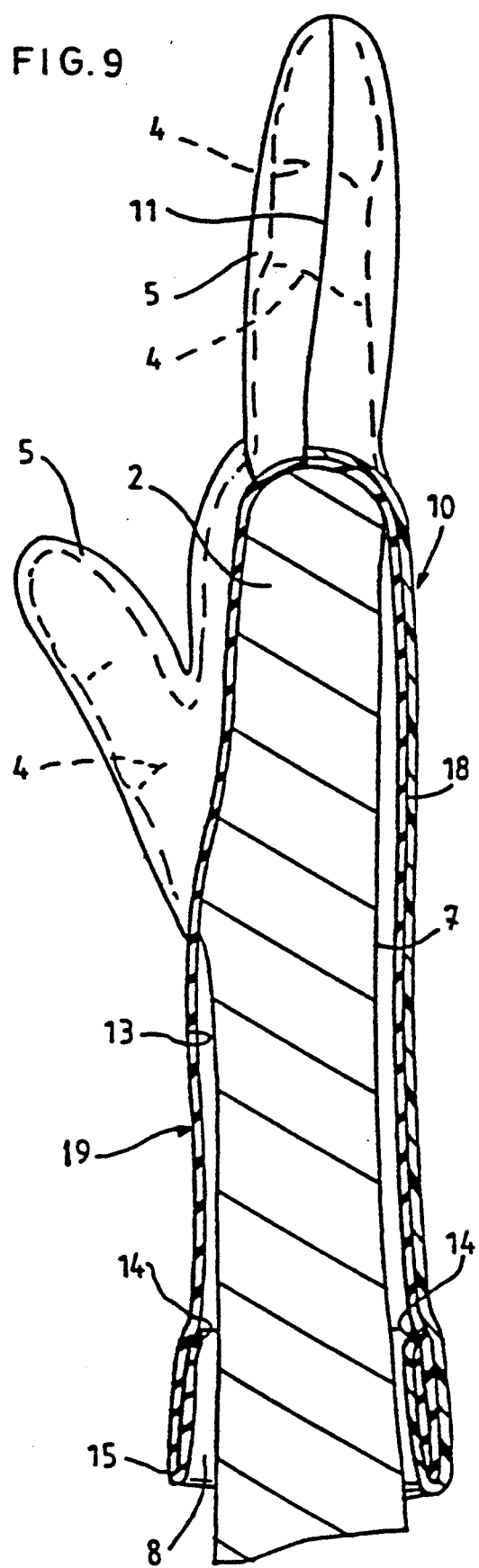

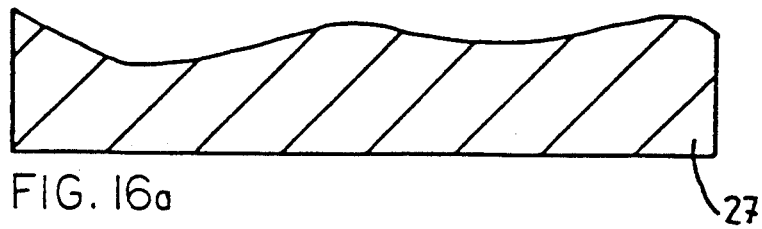
FIG. 16a
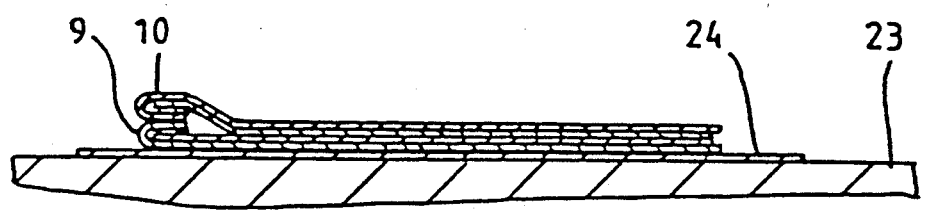
FIG. 16b
FIG. 17
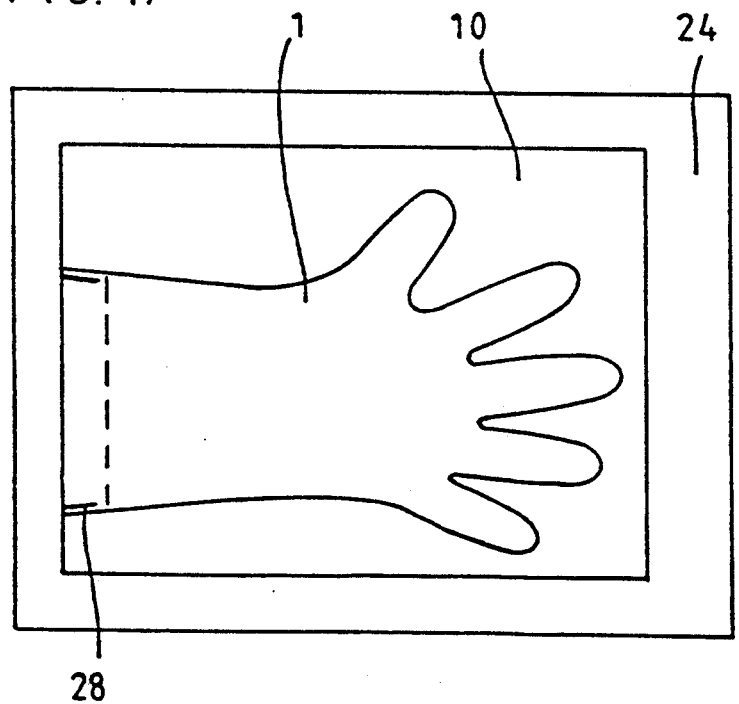

GLOVE

The present invention relates to a glove comprising a front sheet and a back sheet, at least one of said sheets consisting of an inner layer and an outer layer made of polymeric films, said layers being bound to each other.

The use of very thick plastic gloves becomes necessary, when the user is submitted to rather high temperatures, ionizing radiations, highly toxic aggressive chemicals or high mechanical stresses.

The front and back sheets of known plastic gloves, such as described in U.S. Pat. Nos. 3,025,403 and 3,883,749, comprise each an inner layer and an outer layer consisting of polymeric films which are bound to each other on the entire area of the faces facing each other of said layers, so that said layers are integral.

When said gloves are thick, for example, when they have a thickness of about 200 microns, it becomes frequently difficult or impossible for the user to have a good feeling for the fingers.

Another disadvantage of the known plastic gloves provided with polymeric layers glued together is the danger of a complete tear from a little fissure or another defect.

An object of this invention is a thick plastic glove having the ergonomical qualities of a thinner glove.

Another object of the present invention is a glove having a high feeling sensivity, despite its thickness.

Other objects of the present invention are gloves having the following advantages with respect to said known gloves:
easier fitting on a hand;
increased freedom of movements of the hand and particularly the fingers thereof;
improved comfort for the user;
increased security against complete tearing;
lower risk of simultaneous perforation of all the layers;
low probability of having surperimposed pinholes.

The glove according to the invention of the type defined in the first paragraph of this specification is essentially characterized in that faces facing each other of at least two adjacent layers are independent from each other so as to allow relative movements between said two layers.

The glove according to the invention comprises preferably at least two separate layers only bound to each other along their periphery.

In a particular embodiment of the glove according to the invention, the dynamic and static friction coefficient of the faces facing each other of said adjacent layers is of less than 0.80 and more preferably lower than 0.70.

According to a feature of the glove according to the invention, the adjacent layers contain at least one agent allowing said layers to slide on each other or the faces facing each other of the adjacent layers are coated with at least one agent allowing said layers to slide on each other.

Said agent is preferably selected in the group consisting of saturated hydrocarbons, fatty acids, high molecular weight alcohols, metal soaps, waxes fatty acid monoesters, fatty acids partially esterified polyfunctional alcohols, fatty acid bisamides, stearamide and erucamide.

More particularly, said agent which acts as a lubricant is selected among:
solid paraffins (saturated,hydrocarbons) such as polyethylene waxes having a molecular weight comprised between 2,000 and 10,000 and having preferably a melting point of about 65° to 75° C.;
higher molecular weight fatty acids such as stearic, palmitic, myristic, oleic and 12-hydroxy stearic acids;
cetylstearyl alcohol;
stearates of lithium, strontium, calcium, aluminum, barium and lead;
esters of fatty acids and high molecular weight monofunctional alcohols such as waxes from partially saponified montanic acid, esters with $C_{28}$ and $C_{32}$ chains and stearyl stearate;
butyl and octyl stearates;
hydrogenated tallow glycerides, glyceryl monostearates or glyceryl monoricinoleates, esters of sorbitol, ethylene glycol, propylene glycol and pentaerythritol, and
ethylene bisstearoylamide, ethylene bisoleoylamide, $C_{16}$ and $C_{18}$ bisamide, ethylene bisstearoylamide.

Said additive, agent or product is used in most formulations in a proportion of 1 to 2% by weight with respect to the weight of the polymer. These additives, agents or products improve the surface properties of polymers, but may also improve the light stability, resistance to degradation by corrosive agents and to water absorption and the electrical, optical and mechanical properties.

Said additives or lubricants prevent the polymers to have a tendency toward tackiness.

In another particular embodiment of the invention, the faces facing with each other of the adjacent layers are provided with a multiplicity of projections and/or cavities.

Instead of providing a sliding agent within the adjacent layers or in a coating applied on these layers, it is possible, according the invention, to use loose particles which are located between the faces of said adjacent layers, said particles promoting relative movements between said layers.

The adjacent layers may be independent from each other only in the finger area or even only in the neighborhood of the knuckles of said finger area. Of course, said adjacent layers may be independent from each other on the entire area of the faces facing each other, except that said layers are welded together along at least one of their edges.

Other features of the invention will appear in the following detailed description of various embodiments of gloves according to this invention.

In this description reference is made to the attached drawings in which:

FIGS. 5 to 8 are cross-sections similar to that of FIG. 3 showing further embodiments of the invention, and FIG. 9 is a cross-section similar to that of FIG. 2, showing still another embodiment of the invention;

FIG. 16 is a cross-section of the layers shown in FIG. 15 when said layers forming a first sheet are covered with a second sheet, and FIG. 17 is a front view of the layers shown in FIG. 16 when hot pressed.

In these figures, the same elements or parts are designated by the same references.

Figure 1:
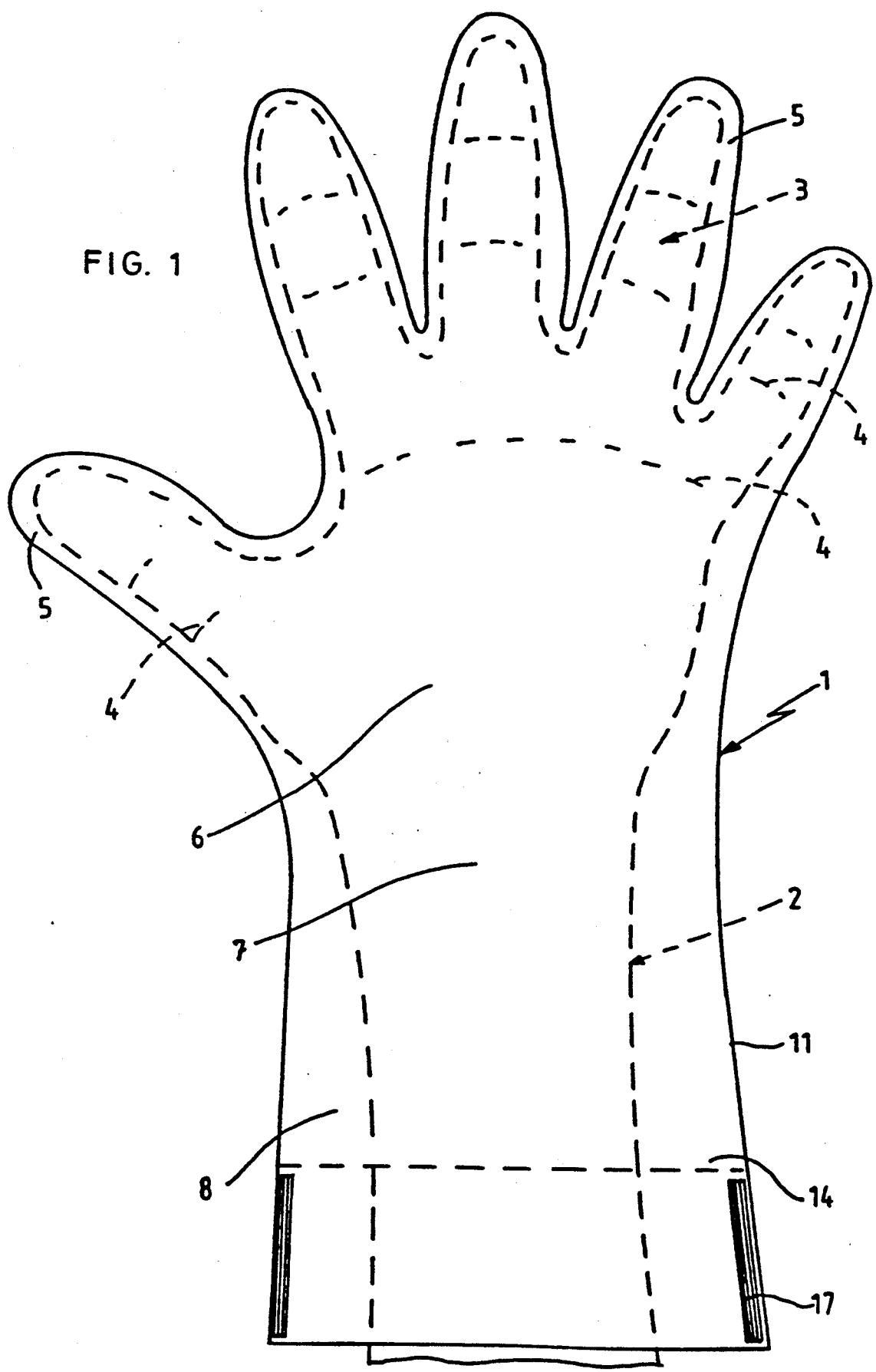
FIG. 1 is a front view of a glove according to the invention.

FIG. 1 shows a glove 1 fitted on a hand 2 shown in dotted lines, with hand fingers 3 and the knuckles 4 thereof.

The glove 1 comprises a finger part 5, a palm part 6, a wrist part 7 and a forearm part 8.

The glove 1 comprises a front sheet 9 and a back sheet 10 which are welded together all along their corresponding edges 11. Each of the sheets 9, 10 consists of an outer layer 12 and an inner layer 13 made of polymeric films which are adjacent to each other and bound together along said edges 11 (see FIG. 2).

Said inner layer 13 and outer layer 12 are also bound to each other by welding (see welding line 14), in the neighbourhood of the end 15 of the glove 1, said end 15 being adjacent to the wrist part 7 or forearm part 8. In fact, the forearm part 8 of the glove 1 is bent inwardly as shown by reference 16, so that said forearm part 8 comprises in fact four layers 12, 13 per sheet 9,10. An additional welding line 17 is provided on the edges 11 of the end 15 of the forearm 8.

The faces of the outer layer 13 and of the inner layer 12 of each sheet, 9, 10, which face each other, are not glued together, but are independent from each other so as to allow relative movements between said adjacent layers.

This relative movement M between said layers 12, 13 can be due to a bending of a finger 4. Due to this movement, two points B,B' of said layers are displaced from each other (see FIGS. 3 and 4).

The layers 12, 13 of each sheet 9,10 are made of a plastic material having low dynamic and static friction coefficients, the latter being of less than 0.80, preferably of less than 0.70.

The layers 12, 13 may be made of various polymeric materials, such as polyolefins particularly polyethylene, polyvinylidene chloride or fluoride, polytetrafluoroethylene, polyacrylate, polyamide, polyimide, silicones, rubber, polyurethane, neoprene and the like. Preferably the layers 12, 13 are made of linear polyethylene having a very low density of at most about 0.91.

Said polymers may contain various antistatic agents, fillers and stabilizers. Such fillers may be asbestos, lead derivatives, bismuth derivatives and other known agents.

The layers 12 and 13 may have the same thickness or different thicknesses. The thickness of each of this layers 12, 13 is preferably comprised between 25 and 300 microns.

If necessary, in order to improve the sliding capacity of the layers 12, 13, these layers may contain an additive or agent which promotes said sliding effect.

The faces of the adjacent layers 12, 13 which face each other and which must be able to move separately from each other may also be coated with at least one agent or product promoting such relative movement. Such coatings 19 are shown in FIG. 5.

Figure 3:
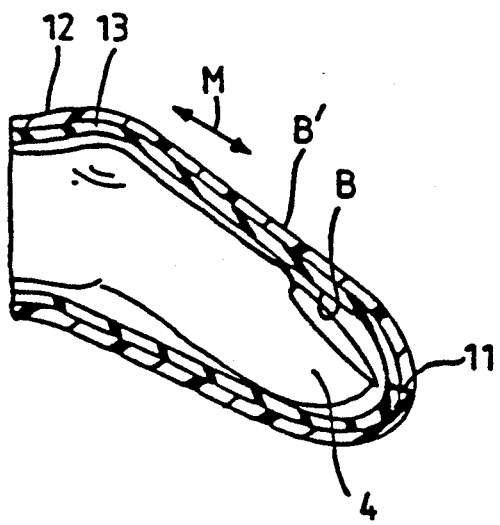
FIG. 3 shows in cross-section adjacent layers of the glove.
Figure 4:
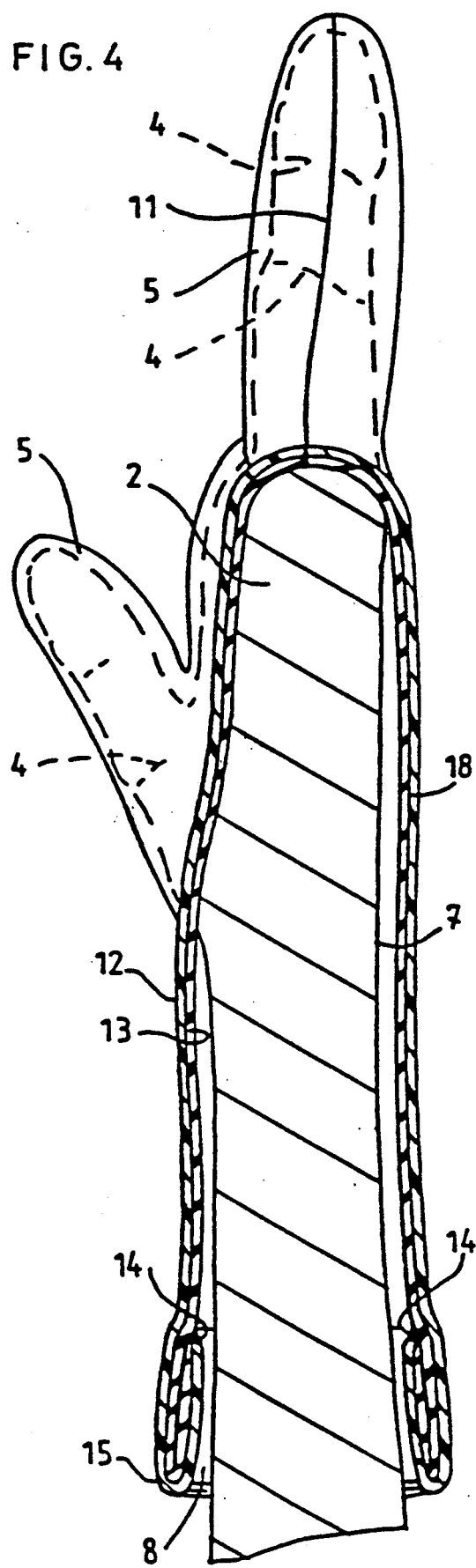
FIG. 4 shows, also in cross-section, the adjacent layers shown in FIG. 3, when bended.
Figure 10:
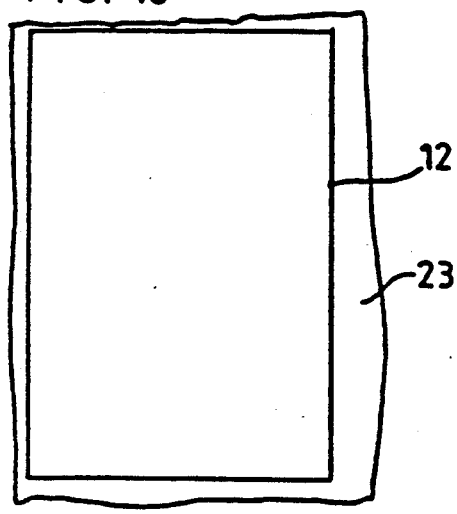
FIG. 10 is a front view of a first step of a process for making gloves according to the invention.
Figure 11:
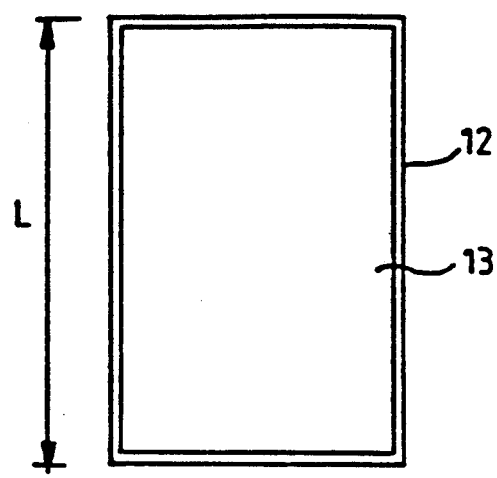
FIG. 11 is a front view of a second step of said process.
Figure 12:
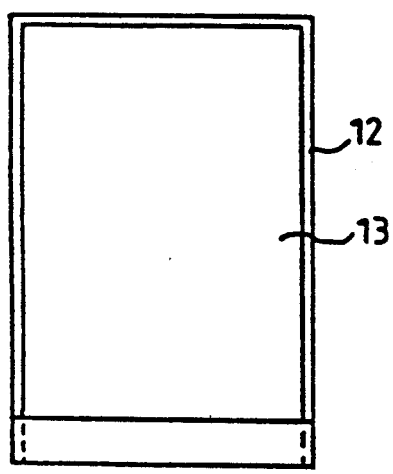
FIGS. 12 and 13 are respectively a front view and a cross-section of layers shown in FIG. 11 when bent.
Figure 13:
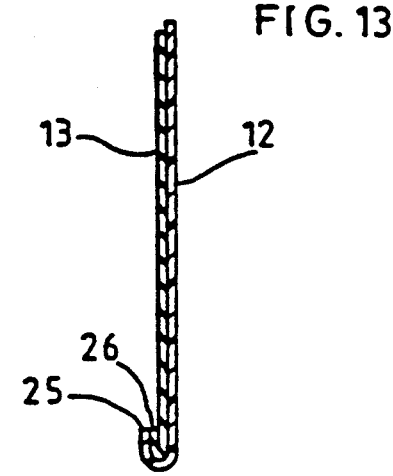
Figure 14:
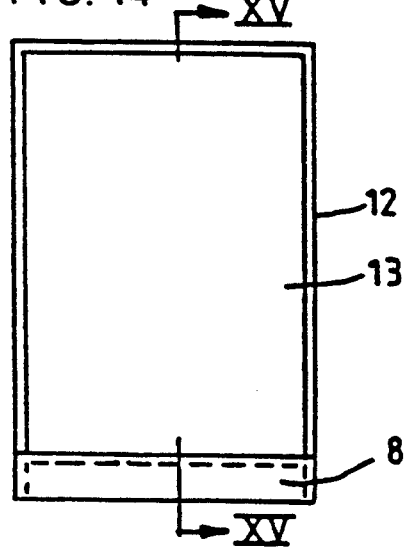
FIGS. 14 and 15 are respectively a front view and a cross-section of the layers shown in FIGS. 12 and 13 when said layers are bound by welding together.

FIG. 4 shows that, when the layers 12, 13 of FIG. 3 are bent, for example in the knuckle areas 4 of the finger part 3, the inner layer 13 is slightly stretched, whereas the outer layer 12 is subjected to a noticeable elongation. In this way, the layers 12, 13 follow closely the movements of the fingers 4 or other parts of the user's hand, so that the feeling sensitivity of the glove is substantially better than that of a previously known glove comprising monolayered front and back sheets.

The additive, agent or product promoting relative movement or sliding capacity are selected among the group consisting of saturated hydrocarbons, fatty acids, high molecular weight alcohols, metal soaps, waxes, fatty acid monoesters, fatty acids partially esterified polyfunctional alcohols, fatty acid bisamides, stearamide and erucamide.

Examples of such additives, agents or products are polyethylene waxes having a molecular weight from 2,000 to 10,000 such as A-C Polyethylene 6 A and 629 A (Allied Chemical Corp, U.S.A.), Epolene E-14P Wax (Eastman Chemical Products, Inc, U.S.A.), stearic acid, myristic acid such as Harwick F-300 (Harwick Chemical Corp, U.S.A.) and Loxiol G20 (Henkel, Inc, U.S.A.), cetylstearyl alcohol, aluminum stearate such as Plymouth SM-03 (Penick, S.B., and Co, U.S.A.), barium stearate such as Witco (Witco Chemical Corp., U.S.A.), cadmium stearate such as Synpro cadmium (Synthetic Products Co., Div.Dart Industries Inc., U.S.A.), calcium stearate such as Lubricant Hoechst VPCaF1 and VPCaF2 (American Hoechst Corp., U.S.A.), lead stearate such as Lubricant Hoechst VPPbF1 (American Hoechst Corp., U.S.A.), partially saponified montanic acid such as Lubricant Hoechst Wax OP (American Hoechst Corp., U.S.A), $C_{28}$–$C_{32}$ chains ester such as Lubricant Hoechst Wax E (American Hoechst Corp., U.S.A.), stearyl stearate such as Loxiol G 30 (Henkel, Inc., U.S.A.), butyl stearate, octyl stearate, glyceryl monostearate, glycerol monoricinoleate such as Loxiol G 10 (Henkel, Inc, U.S.A.), fatty acid glycerol monoesters such as Lubricant Hoechst VP FE 2 (American Hoechst Corp., U.S.A.), ethylene bis-stearoylamide such as Interstab G-8257 (Interstab Chemicals, Inc., U.S.A.) and $C_{16}$–$C_{18}$ chains bisamide such as Lubricant Hoechst Wax C (American Hoechst Corp., U.S.A.).

Preferred additives are stearamide and erucamide.

FIG. 6 shows two layers 12, 13 of a sheet 9, 10, the layer 13 being provided with a multiplicity of projections 20 on a face 18 which is adjacent to the layer 12. Said multiplicity of projections promote relative movements between said layers 12, 13. Instead of projections, the layers 12, 13 may also be provided with cavities.

FIG. 7 shows two layers 12, 13 of a sheet 9, 10 of a glove 1. Between the faces 18 facing each other of said adjacent layers 12, 13, loose particles 21 are located so as to promote relative movements between said layers 12, 13. Such loose particles may be, for example, talc particles having a size lower than 50 microns.

FIG. 8 shows two layers 12, 13 of a sheet 9, 10 which are welded together along their edges 11. Between the faces 18 facing each other of said adjacent layers 12, 13, a sliding film 22 is inserted.

Said film which may be an aluminum or polytetrafluorethylene film is preferably bound to the layers 12, 13 in the neighbourhood of their welded edges. Such a film 22 allows to obtain a static and dynamic friction coefficient of said faces 18 of less than 0.80.

Figure 2:
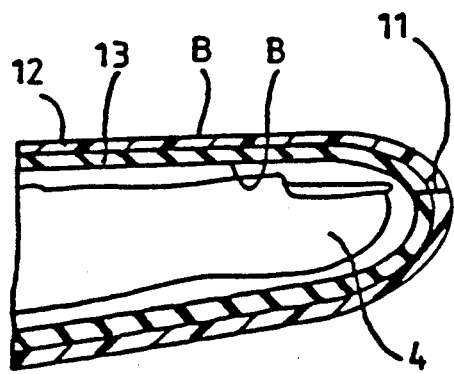
FIG. 2 is a cross-section along the line II—II of FIG. 1.

FIG. 9 shows in cross-section a glove 1 similar to that represented in FIG. 2, except that the sheet 9 intended to cover the palm part 6 of a hand comprises only one layer 13 made of a polymeric film. Said sheet 9 may comprise only one layer 13, since it is only submitted to bending and not to stretching.

A process for making gloves according to the invention is schematically shown in FIGS. 10 to 17.

A first layer 12 is deposited on a support 23. This layer 12 may be made of a polyethylene having a density of about 0.91 and containing from 30 to 80 % by weight of particles of bismuth oxide of the formula $Bi_2O_3$. Said particles have a size lower than 40 microns, preferably lower than 10 microns and more preferably lower than 5 microns. The bismuth oxide diminishes the friction coefficient to a value lower than 0.7. Instead of $Bi_2O_3$, particles of bismuth, other bismuth oxide, bismuth hydroxide and bismuth salts may be used.

The first layer 12 has a thickness of about 80 microns.

Preferably, the support 23 is covered with a smooth paper sheet 24 on which said layer 12 is deposited (see FIG. 16).

On this layer 12, a second layer 13 which has the same characteristics as those of the layer 12 is deposited. Said layer 13 has a length L which is somewhat lower than that of the layer 12 (see FIG. 11), so that when one end 25, 26 of said layers 12, 13 is bent, the layer 12 covers the end 25 of said layer 12 (see FIGS. 12 and 13).

Figure 15:
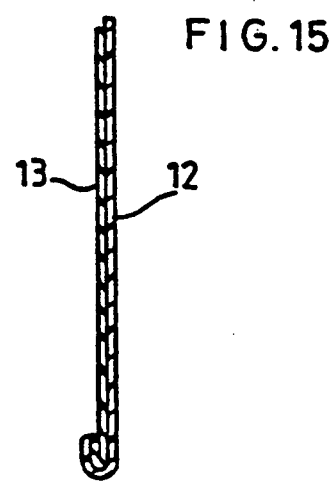

When the layers 12, 13 are bent at one (25, 26) of their ends, these layers 12, 13 are welded together in the neighbourhood of said ends 25, 26. The welding line 14 is shown in dotted lines in FIG. 14. FIG. 15 shows a cross-section of the layers 12, 13 represented in FIG. 14 along the line XV—XV.

Said layers 12, 13 form a first sheet 9. Another sheet 10, which is identical to said first sheet 9, is deposited so that the ends 25, 26 are adjacent (see FIG. 16).

Then a hot pressing machine 27 is pressed on said sheets 9, 10 so as to form welding lines 11. Said welding lines 11 bind the sheets 9, 10 as well as the layers 12, 13 of each sheet together. The welding lines 11 define the form of the desired glove 1.

Preferably the hot pressing machine forms also further welding lines 28 in the neighbourhood of the ends 25, 26 of the sheet 9,10 and in the neighbourhood of the welding line 11, so as to avoid any risk of tear when fitting the glove on.

Gloves 1 made by the above described process may be used for the right hand or for the left hand, without difficulty.

EXAMPLE

The following example illustrates the composition of a glove according to this invention.

A glove according to FIGS. 1 to 4 has been manufactured in the manner described above by using films of polyethylene having a density of about 0.900–0.920 and a thickness of about 100 microns, said films containing 0.4% by weight of erucamide. The friction coefficient of the surfaces facing each other of the sheet was of 0.70.

The gloves 1 according to the invention are suitable for domestic, medical, surgical, or industrial uses. They are particularly suitable for surgical operations and medical examination.

We claim:

1. Glove comprising a front sheet (9) and a back sheet (10), at least one of said sheets having an outer layer (12) and an inner layer (13) made of polymeric films, said layers being permanently bound to each other along their periphery, characterized in that contacting faces (18) of said inner and outer layers (12, 13) are independent from each other so as to allow relative movements (M) between said inner and outer layers (12, 13) and that the dynamic and static friction coefficient of the contacting faces (18) is less than 0.80.

2. Glove according to claim 1, in which said friction coefficient is lower than 0.70.

3. Glove according to claim 1 characterized in that the adjacent layers (12, 13) contain at least one agent allowing said layers to slide on each other wherein said agent is selected in the group consisting of saturated hydrocarbons, fatty acids, metal soaps, fatty acid monoesters, fatty acids partially esterified polyfunctional alcohols, fatty acid bisamides, stearamide and erucamide.

4. Glove according to claim 1, characterized in that the adjacent layers (12, 13) contain at least one agent allowing each layer to slide on each other wherein said additive consists of particles of bismuth, bismuth oxides, bismuth hydroxides or salts of bismuth.

5. Glove according to claim 4, characterized in that said additive is the bismuth oxide of the formula $Bi_2O_3$.

6. Glove according to claim 4, characterized in that said particles have a size lower than 40 microns.

7. Glove according to claim 6, characterized in that said particles have a size lower than 5 microns.

8. Glove according to anyone of the claim 4, characterized in that the layer contains 30 to 80% by weight of said particles.

9. Glove comprising a front sheet (9) and a back sheet (10), at least one of said sheets having an outer layer (12) and an inner layer (13) made of polymeric films, said layers being bound to one another along their periphery, characterized in that contacting faces (18) of said inner and outer layers (12, 13) are independent from each other so as to allow relative movements (M) between said inner and outer layers (12, 13), the adjacent layers (12, 13) contain at least one agent (19) allowing said layers (12, 13) to slide on each other.

* * * * *